(12) United States Patent
Nour

(10) Patent No.: US 8,684,903 B2
(45) Date of Patent: Apr. 1, 2014

(54) THERAPEUTIC AND SURGICAL TREATMENT METHOD FOR PROVIDING CARDIOPULMONARY AND CIRCULATORY ASSIST DEVICE

(75) Inventor: Sayed Nour, Chaville (FR)

(73) Assignees: Gui Fu Wu, Guangzhou (CN); Pierre Chastanier, Paris (FR)

( * ) Notice: Subject to any disclaimer, the term of this patent is extended or adjusted under 35 U.S.C. 154(b) by 462 days.

(21) Appl. No.: 13/045,760

(22) Filed: Mar. 11, 2011

(65) Prior Publication Data

US 2012/0232331 A1    Sep. 13, 2012

(51) Int. Cl.
*A61N 1/362*    (2006.01)
*A61N 1/00*    (2006.01)
*A61B 5/02*    (2006.01)

(52) U.S. Cl.
USPC ............... 600/16; 600/15; 600/485; 600/504

(58) Field of Classification Search
USPC ...................... 600/15–16, 485, 504
See application file for complete search history.

*Primary Examiner* — Nicole F Lavert
(74) *Attorney, Agent, or Firm* — Carter, DeLuca, Farrell & Schmidt, LLP

(57) ABSTRACT

The present disclosure relates to a therapeutic method for improving the hemodynamics, the overall microcirculation in organs, and the restoration and preservation of deficient endothelial function in a patient, the method includes maintaining blood circulation in the patient's veins and arteries and temporarily relieving the heart of its pumping function. Relief may be accomplished by increasing the preload of the right ventricle so as to improve oxygenation of the myocardium and its contractility, reducing and diffusing regular pulsations in the proximity of the aortic root so as to improve the hemodynamics of the left ventricle of the heart, and/or mechanically stimulating the endothelium by shear forces so as to reduce systemic and pulmonary afterload.

16 Claims, 3 Drawing Sheets

THERAPEUTIC AND SURGICAL TREATMENT METHOD FOR PROVIDING CARDIOPULMONARY AND CIRCULATORY ASSIST DEVICE

TECHNICAL FIELD OF THE INVENTION

The present disclosure relates to a novel therapeutic technique and method of providing mechanical circulatory assistance using a circulatory assist device (CAD) that is minimally invasive. The CAD improves hemodynamics and microcirculation, and restores the endothelial function when it is insufficiently stimulated, particularly for a patient suffering from congestive heart failure (CHF).

STATE OF THE PRIOR ART

Cardiovascular disease (CVD) is the first cause of mortality in developed countries, responsible for 1 death every 35 seconds and the estimated global annual cost is $403.1 billion according to recent statistics from the United States (Circulation. 2006; 113: e85-e151).

Congestive heart failure (CHF), has been defined by the NIH, as the new epidemic in the USA, affecting more than 5 million new cases per year with a 5-year survival rate of less than 50%.

Current therapies for CHF patients include medicinal provision of drugs (e.g. cardiac glycosides, diuretics, AC inhibitors, anticoagulant, etc.). However, medicinal therapies are usually insufficient necessitating complementary cardiac supports e.g., mechanically with CAD and/or biologically with surgical procedures like aortomyoplasty, cardiomyoplasty, cellular therapy, heterotopic heart transplants, and othrotopic heart transplants as un ultimate procedure.

A mechanical cardiac assist device (CAD) is usually used temporarily until the patient's hemodynamics improve, or as a bridge prior to a heart transplant.

Permanent replacement of the heart with an artificial heart is still a work in progress with current technologies having a short life expectancy. Thus, the artificial heart is primarily used as a bridge to transplant for patients with biventricular failure. Furthermore the large size of an artificial heart limits its applications in specific categories, regarding body surface area (1.9+/−0.22 $m^2$), sex (95% men) and age (practically 0% children) *Ann Thorac Surg.* 2009; 87(1):124-9.

Present arts of cardiac assist devices can be classified in two categories:

A) Devices that increase coronary blood flow during diastole, in order to improve the oxygenation and thus the performance of the myocardium. This category includes the intra-aortic balloon pump (IABP) and to the enhanced external counterpulsation pump (EECP). These devices must be synchronized with the heartbeat and unsuitable in case of cardiac arrhythmias; and B) Devices that unload and bypass the heart pump: either partially as achieved by left ventricular assist devices (LVAD), right ventricular assist devices (RVAD), and by extracorporeal membrane oxygenation (ECMO); or completely like with biventricular assist devices, extracorporeal circulation (CPB), heterotopic heart transplant.

It should be emphasized that ECMO partially deviates some of the venous blood to an external membrane oxygenator. ECMO does not completely unload the right ventricle (RV) and that may explain its successful applications in pediatrics patients who are more frequently vulnerable to RV failure.

Unfortunately current therapies for CHF still represent cost-effectiveness dilemma for health care systems in modern societies associated with high cost, morbidity and mortality.

Most probably CAD could aggravates hemodynamics leading to multiple organ failure and death due to factors directly linked to devices themselves or indirectly due to patients related factors as follows:

I) Device Related Factors:
 a) Concept and design drawbacks: A CAD is typically a lumped model constructed according to laws of physics for driving a Newtonian compressible fluid inside a closed pressurized hydraulic circuits, implementing rigid tubes with fixed diameter. Meanwhile in practices a CAD is confronted with a non-Newtonian fluid (blood, running in flexible vessels with different geometries. This confrontation between two opposite pressurized hydraulic circuits (CAD and circulation) creates a vicious circle of momentum energy losses manifested clinically by increased vascular resistances with endothelial dysfunction (e.g. hemorrhage, thromboembolism, inflammatory response, apoptosis, etc.), up till multiple organ failure.
 b) driving forces drawbacks, more precisely, roller or centrifugal pumps are usually used to circulate and perfuse blood between the patient and the external circuit most commonly in a steady flow mode of perfusion.

Unfortunately even with biocompatible materials the effect of sucking and pumping fragile fluid like blood mechanically (e.g. with impellers, propellers, or pulsed reservoir), inside narrow rigid conduits and tubes create zones of turbulence and vortices with important energy losses (e.g. hemolysis).

c) Installations systems drawbacks: usually conduits, tubes, and cannula made of biocompatible materials (e.g. PVC®, Dacron®, PTFE®,), are used for connection between patient and CAD. In addition those conduits need to be securely stitched to cardiovascular tissues, diverted and under the skin (tunnelization) to allow proper chest closure, then to be de-aired before and checked for leakage or gas emboli before finally connected to their corresponding CAD.

Furthermore, the distance between a CAD and the patient's inlet/outlet sites gives rise to dead space, creating an additional important momentum energy losses zone.

Finally, the procedures for installing such devices need to be carried out by experienced surgeons in specialized centers on patients who are fragile, and who have usually already been operated on several times in the past, increasing the risks of morbidity and mortality (e.g. hemorrhages, vascular complications, infections, multiple organ failure).

II) Patient Related Factors:
The aggravating factors inherent to the patients themselves can be of several kinds such as:
 a) Age, sex: most CAD devices are unsuitable for patients with small body surface area (e.g. children, female) since more than 80% of CAD devices are designed for body areas of more than 1.5 square meters ($m^2$), i.e. corresponding to adult heart patients. In addition CAD are generally first designed for the management adult heart diseases and then miniaturized to cope with pediatric populations. However, pediatric patients are more vulnerable to hemodynamic disturbances caused by right heart failure due to congenital anomalies and they are vulnerable to vascular complications caused by small vessels geometries in content. Adults usually suffer from ischemic left heart diseases with atherosclerotic vessels and they are therefore more vulnerable to vascular complications.

b) Etiology: Fate of CHF patients with severe right ventricular (RV) failure (CVP>16 mmHg) is worse than those patients with left heart sided pathologies. Current therapies employing CAD to treat CHF patients with severe RV failure still exhibit a high mortality rate (65-95%), most probably due to insufficient understanding of the great difference between the right and left heart circuits, particularly the biophysics and physiopathological demands.

c) Miscellaneous: Finally, the shortage of donors, immunosuppressive drugs drawbacks (e.g. malignancy); coronary atherosclerosis, follow up costs and surgical complications, all contribute to limiting the generalization of such treatments in practice.

SUMMARY OF THE INVENTION

The present disclosure is directed to cardiac orthosis to support and restore an organ function, rather than a prosthesis that replaces an organ. The present disclosure also seeks to remedy the drawbacks of the state of the art and includes a therapeutic method for providing cardiopulmonary and circulatory assistance.

Use of the devices and methods of the present disclosure in patients suffering from congestive heart failure (CHF), as a global circulatory assist device, could restore the lost and/or weaken myocardial function, reduce the necessity of heart transplantation, or at least to be used as a more efficient bridge with fewer complications.

To do this, in a first aspect, the proposed therapeutic method for improving hemodynamics, for improving overall microcirculation in organs, for restoring and preserving deficient endothelial function in a diseased human being, the method comprising the following steps: maintaining the circulatory flow dynamics of blood in the patient's systemic and pulmonary circulation (endocardium, veins, arteries and capillaries); and temporarily relieving the heart of its pumping function.

According to the present disclosure, the method consists in using at least one device external to the patient's body and connected by at least a pipe and/or a specific connection element to:

increase the preload of the right ventricle so as to improve oxygenation of the myocardium and so as to improve its contractility; and/or unload the left ventricle and diffuse regular pulsatile flow in the proximity of the aortic root so as to improve the hemodynamics of the left ventricle of the heart; and/or stimulate the endothelium mechanically by shear stress enhancement so as to release several mediators of endothelial vasodilators like nitric oxide (NO), to reduce the systemic and pulmonary afterload.

Thus, and advantageously, one method of the of the present disclosure makes it possible to improve the microcirculation of the main vital organs of the patient by means of a plurality of endothelial vascular vasodilator mediators that are secreted in particular in response to the application of quasi-physiological tangential forces of shear stress against the patient's endothelial walls.

More precisely there are three manners to stimulate the endothelium:

Direct internal endothelial stimulation that will be induced by an intrapulmonary artery pulsatile catheter device.

Indirect internal endothelial stimulations with a pulsatile perfusion flow generated by a pulsatile tube device at the left heart side.

External stimulation (pulsatile suit) at the right heart side endothelial.

In other words, with said device(s) in place on the patient, it is found advantageously that there is an improvement in the microcirculation of organs as a result of at least one novel vasodilator mediator that is triggered by applying quasi-physiological shear forces to the patient's endothelial walls.

According to an advantageous aspect of the invention, the regular pulsations created in the proximity of the aortic root are synchronized with the patient's electrocardiogram.

Furthermore, the disturbances of the angiogenesis-apoptosis interdependency processes that are degraded in the patient are reestablished (and restored).

Furthermore, the step of temporarily relieving the heart consists in relieving the left ventricle.

More precisely, in one embodiment of the present disclosure, said relief is performed starting from the apex of said left ventricle (LV).

In a second embodiment of the invention, said LV relief is performed by a transeptal left atrial approach.

In one exemplary embodiment of the present disclosure, said pulsations are diffused in the proximity of the aortic root by inserting a perfusion cannula in the aortic root or in the subclavian artery, by a percutaneous approach, optionally assisted by remote guidance such as echocardiogram guidance, or any other type of remote guidance.

Functional relief of the left ventricle maybe performed by inserting a cannula at the LV apex via a percutaneous approach, the insertion preferably guided by echography (remote guidance) to the apex of the heart in the fifth intercostal space or in a large systemic vein such as the right subclavian vein, in case of left atrial vent with a transeptal approach.

In one advantageous aspect at the beginning of the surgical procedure, the connection pipe(s) is/are filled with preferably heparinized physiological saline or with any equivalent liquid so as to avoid any form of gaseous embolism during or after said method.

More specifically, a pulsatile intrapulmonary catheter is put into place by a percutaneous intravenous approach so as to reduce pulmonary afterload and to improve myocardial microcirculation and contractility.

According to another aspect of the present disclosure, a pulsatile suit is put into place on a portion of the patient's body so as to improve the functioning of the right ventricle (its contractility) and also the hemodynamic, of said patient. The contractibility of the ventricle as well as the organs microcirculation of the patient are also improved.

BRIEF DESCRIPTION OF THE FIGURES

Other characteristics, details, and advantages of the invention appear on reading the following description given with reference to the accompanying figures, in which.

Figure 1:
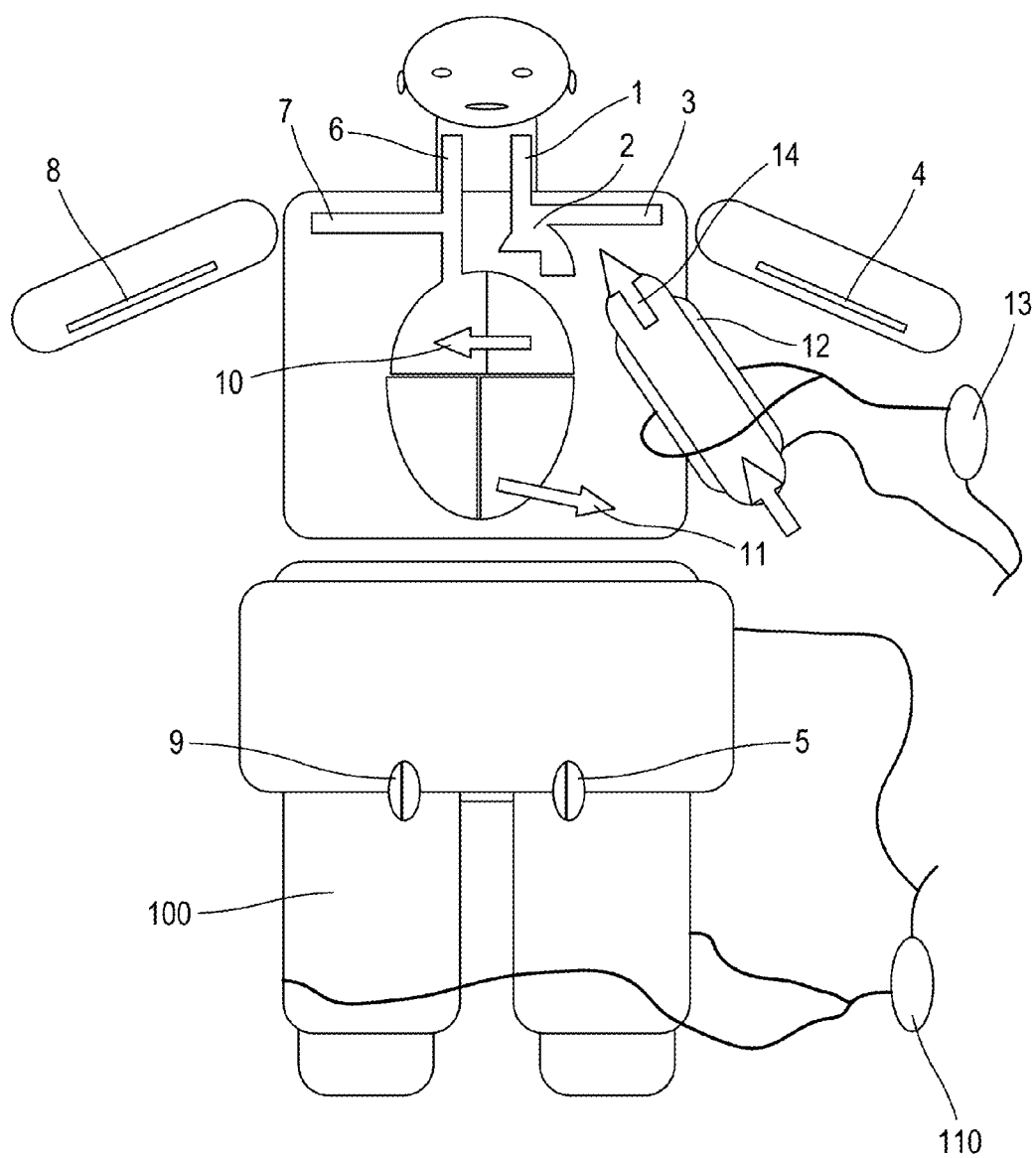
FIG. 1 is a diagrammatic section of equipment in a first aspect of the invention.

For greater clarity, elements that are identical or similar are identified by identical reference signs in all of the figures.

DETAILED DESCRIPTION OF AN EMBODIMENT

The present invention is based on a main concept (Think endothelial) and on a new hemodynamic theory entitled (Flow and Rate) that seeks to improve hemodynamics, organs microcirculation, restore and preserve the endothelial function by maintaining shear stress-mediated endothelial function with circulatory dynamics forces e.g., pressurized flow and shear rate.

As is known, human being is a multicellular organism in which cellular biology performs a main role in terms of development, maintenance, proper operation, and also failure of vital organs.

Maintaining good operation of organs by means of general microcirculation in the organs constitutes a characteristic effect of the invention.

Momentum transfers in hydraulic circuits depend on driving forces, resistances, viscosity and conduits. Our circulatory system is a closed pressurized hydraulic circuit and that is lined units interior with endothelial cells. In general hemodynamic forces created by pressurized blood flow and shear rates are constantly stimulating endothelial function (e.g. vascular tone, embryogenesis, organogenesis, immune systems, inflammatory response, atherosclerosis, thrombosis, etc) since intra-uterine life.

In circulatory systems, the heart and peristaltic arteries represent the main circulatory driving forces, otherwise accessory forces (e.g. respiratory pump, muscle pump, gravity, atmospheric pressure, oncotic pressure, skin baroreceptors) are necessary to move up the steady blood flow at the right heart side. *Nour S, Asian Cardiovasc Thorac Ann* 2009; 0:1-6. Meanwhile vascular resistances depend on vascular tone and vessels elasticity that are controlled mainly by shear stress-mediated endothelial function. Endothelium controls vasoconstriction (e.g. catecholamines), vasodilatation with several mediators like nitric oxide (NO) and vascular conditions with several processes like atherosclerosis and angiogenesis-apoptosis interdependency.

Disturbed flow dynamics caused by pump failure and/or elevated vascular resistances, could induce endothelial dysfunction, which is a major predisposing factor to hemodynamic troubles, circulatory disorders (e.g. diabetes, arterial hypertension, etc) and life-threatening conditions (e.g. cardiogenic shock, multiple organ failure). As a symbolic example, right ventricular (RV) failure can occur either due to elevated pulmonary vascular resistances caused by pulmonary oligemia, pulmonary hyperemia; or due to RV pump failure caused by ischemia, congenital anomalies, arrhythmia, valvulopathy, accessory circulatory driving forces failure (e.g. Fontan failure).

The present disclosure proposes clinical applications of these tangential forces of shear stress in order to regulate the endothelial function so as to improve the hemodynamic of patients, the overall microcirculation of organs, and, when it has failed, to reestablish normal operation of the cardiac pump 10, 11 in a manner that is as physiological as possible, without replacing any organ and without any traumatic intrusion, to provide a method that is as minimally invasive as possible.

Healthy microcirculation is essential for cell metabolism and is normally controlled by hemorheological factors and by the circulatory driving forces.

Normally microcirculation depends directly on a plurality of vasodilators mediators secreted by the endothelium, such as nitrogen monoxide (NO), prostacyclin, or phosphodiesterase-5 inhibitors.

Dependency of microcirculation on tangential forces of shear stress-mediated endothelial function, could be achieved in two manners: a) increased pulse pressure rather than shear rate according to Newton's $2^{nd}$ law; or b) increased shear rates at the inner boundary walls rather than pulse pressure according to Bernoulli'$3^{rd}$ equation.

Under normal hemorheological condition, microcirculation behavior approaches that of Newton's law. A symbolic example observed in athletics, high physical performance, which means shear stress-mediated endothelial function, could be achieved with slow heartbeat (shear rate) and increased stroke volume (pulse pressure).

In contrast, in any abnormal hemorheological state, microcirculation presents behavior that approaches that of Bernoulli's law, as interpreted by the Fahraeus-Lindqvist effect in which plasma stuck at the inner vascular boundary layers while erythrocytes move faster at the center. This could explain absence of cyanosis in anemic patients with low hematocrite, unlike those patients with high hematocrite, as erythrocytes aggregations at microcirculation induce cyanosis with clinical signs finger clubbing (drumsticks fingers).

The present invention is a new therapeutic approach of clinical application of shear stress in consideration with the circulatory system's biophysics and pathophysiological conditions and laws of fluid mechanics as follows:

I. At the left heart side, a shear stress-mediated endothelial function must be induced according to Newton's principles by maintaining and that is could be afforded by (Pulsatile tube's 12) as a LVAD to deliver and maintain an almost physiological systemic arterial pulse pressure.

II. At the right heart side both two principal concepts of physics laws (Bernoulli, Newton) in addition to the gravity effect as well (e.g., Pascal's Law) must be considered to deliver a shear stress-mediated endothelial function, and without changing the physiological remodeling of the right heart circuit (e.g. Laplace). Thus intravascular clinical application of shear stress according to the Newton's law means with pulse pressure must be avoided as it could induce serious hemodynamic conditions like irreversible pulmonary remodeling (e.g. Eisenmenger syndrome), post coronary surgery venous grafts disease. This explains failure of current pulsatile CAD in case of RV failure, an additional dilemma for CHF therapies with RV failure.

Contrarily to current evidence of high mortality of CHF patients associated with right heart failure, the invention of the present disclosure consider the right heart as a physiological backup for management of almost all types of hemodynamics and circulatory disorders including CHF patients.

The right heart circuit contains >64% of blood volume surrounded by an important mass of endothelial cells. This natural stock of blood volume and endothelial mass can be stimulated by a proper pulsatile CAD, adaptable for right heart circuit's biophysics and physiopathology, for inducing shear stress-mediated endothelial function enhancement.

The influence of right heart on hemodynamics is observed by the immediate postnatal drop of the pulmonary vascular resistances, triggered by external shear stress-mediated endothelial function induced by the respiratory pump (creating an indirect internal pulse pressure closer to Newton's law).

Another example is observed in patients in the squatting position during cyanotic spells of Tetralogy of Fallot (TOF), that increases the systemic vascular resistances, and increases the intrapulmonary flow and shear rates in a retrograde manner through the misaligned VSD to lower the pulmonary vascular resistances, followed by global hemodynamic improvement. The increased intrapulmonary shear rate that can be induced by adrenaline injection as well during cyanotic TOF spells, provides shear stress-mediated endothelial function approaching Bernoulli's law.

Therefore, the invention of the present disclosure consider that the right heart dominates left heart and hemodynamic, since from intrauterine life, most probably through pulmonary vascular resistances.

Reduction of pulmonary vascular resistances is an immediate target for hemodynamic improvement that can be achieved directly by shear stress-mediated endothelial function enhancement as follows: a) an intrapulmonary shear rate enhancement device (pulsatile catheter); or externally by the (pulsatile suit device 100).

With respect to the right heart 5, different remodeling zones (*Dr. Nour. Asian Cardiovasc Thorac Ann* 2009; 0:1-6): shear stress stimuli at the compliant pulmonary artery (PA) zone (zone5), can be induced with a small size pulsatile catheter adaptable to the pulmonary trunk geometries for shear rates enhancement at the inner boundaries layers, irrespective of heartbeat without obstructing the right ventricular outflow tract.

Meanwhile at the superficial venous capacitance (zone 1) shear stress enhancement could be achieved externally with the (pulsatile suit 100).

An improvement in hemodynamics and overall microcirculation has been observed by application of shear stress mechanical stimuli at the right heart endothelial stock in animal models and healthy volunteers, using prototypes of pulsatile catheter, and pulsatile suit 100 (mask and trouser), as follows:

A) Animal Models (creation of a cardiogenic shock state in neonate piglets):

I. An intrapulmonary artery pulsatile catheter was inserted in animal models of acute myocardial ischemia: Twelve piglets were given either intrapulmonary pulsatile catheter treatment (P: n=6) or non-pulsatile (NP: n=6) treated with nitrates after 1 h of permanent left anterior descending coronary artery ligation. In group P catheter was pulsated intermittently over 1 h at 110 bpm, irrespective of heart rate (73±16 bmp), vs. nitrates (7±2 μg/kg/min) in group NP. Results: animals survived ischemia for 2 h in group P vs. 93±30 min in group NP. Hemodynamics and cardiac output (CO) were significantly better in group P compared to group NP: CO was 0.92±0.15 vs. 0.52±0.08 (L/min) respectively. Lower myocardial apoptosis (0.66±0.07) were observed in P group compared to group NP (4.18±0.27). Vascular resistances (dyne.sec/cm-5.kg-1) were significantly lower (P<0.01) in group P vs. group NP: pulmonary resistance was 119±13 vs. 400±42, and systemic resistance was 319±43 vs. 1857±326, respectively. Myocardial endothelial NO synthase mRNA expression was higher in group P (0.90±0.09) than in group NP (0.25±0.04; P<0.01).

II. Intrapulmonary pulsatile catheter in acute arterial pulmonary hypertension (PAH): Twelve piglets were given either intrapulmonary pulsatile catheter (P: n=6) or non-pulsatile (NP: n=6) Tadalafil treatment. Both groups underwent aorto-pulmonary surgical shunt during 1 h then removed. Over a second 1 h period: in group P, an intrapulmonary artery catheter, was pulsated intermittently at 110 bpm, irrespective of heart rate (90.6±10.74 bmp). In group NP, Tadalafil were given orally (1 mg/kg). Results: hemodynamic and cardiac output (CO) were significantly better in group P compared to group NP: CO was 0.56±0.26 vs. 0.54±0.11 (L/min) respectively. Mean pulmonary artery pressure (PAP) was significantly dropped (P<0.01) in group P compared to group NP: PAP 9.6±2.97 vs. 32.2±5.07 respectively. Vascular resistances (dyne.sec/cm$^{-5}$.kg$^{-1}$) were significantly lower (P<0.01) in group P vs. group NP: pulmonary resistance was 85±42.12 vs. 478±192.91, and systemic resistance was 298.8±172.85 vs. 1301±615.79, respectively.

III. Pulsatile trouser (with integrated belt) tested in acute right ventricular failure model: Twelve neonate piglets, were given either pulsatile trouser (P:n=6), or non-pulsatile (NP:n=6) treatment. Both groups underwent acute RV failure by pulmonary valve avulsion. Management started once severe hemodynamic deterioration establishment (48.1±24.5 min): in group P, a pulsatile trouser, connected to a pneumatic driving force was pulsated intermittently at 40 bpm, irrespective of heart rate (104±27 bmp). In group NP, Tadalafil were given orally (1 mg/kg), IV fluids and adrenaline (0.3 μg/kg). Results: by the end after 1 h of therapy, hemodynamic and cardiac output (CO) were significantly better in group P compared to group NP: CO was 1±0.2 vs. 0.7±0.2 (L/min) respectively. Mean RV pressure (RVP) and pulmonary arterial (PAP) pressure were significantly dropped (P<0.01) in group P compared to group NP: mean RVP was 16±6 vs. 24±2 and mean PAP was 22±1 vs. 31±2 (mmHg) respectively. Vascular resistances (dyne.sec/cm$^{-5}$.kg$^{-1}$) were significantly lower (P<0.01) in group P vs. group NP: pulmonary resistance was 174±60 vs. 352±118, and systemic resistance was 611±70 vs. 1215±315, respectively.

B) Clinical volunteers:

I. Pulsatile Trouser (with integrated belt) was tested in healthy adult volunteers (n:6), were subjected to a low pressure (1.2 bars) fixed trouser pulsations(60 bpm) and without synchronization of heartbeat (72±17 bmp). Results: after 20 min of peripheral microcirculation was measured with laser flow meter (Perimed®-PeriScan PIM 3 System) at the tip of finger was significantly improved: 93.5±31.3 vs. 222.4±35.8(p<0.003).

II. Pulsatile mask was tested in twenty healthy volunteers from both sex (age: 19-68 ys), subjected to 20 minutes of low pressure (0.2-0.6 bars) pulsatile mask, synchronized with diastolic heart rate. Results: hemodynamics and cerebral blood flow was significantly improved (p<0.05), as manifested by Doppler flow measured at the common carotid artery: carotid output: 246±41.73 vs. 294±50.42 (ml/min), and velocity 18±2.4 vs. 21±2.8 (cm/sec). Microcirculation measured with laser flow meter (Perimed®-PeriScan PIM 3 System) from the tip of the nose was 45.5±14.6 vs. 89.2±31.1 (p<0.001); and from the mandibular angle (measured with Perimed®-PeriFlux System 5000), was 28±12.5 vs. 87±35.2 (p<0.05).

These aforementioned summarized animal models results, demonstrate the efficiency of the right heart endothelial reservoir as a physiological therapeutic backup compared to optimum traditional therapies in addressing acute cardiogenic shock state.

The pulmonary endothelium, stimulated with a small size pulsatile catheter that can be introduced intravenously and percutaneously, opens a new era in cardiology as almost all types of ischemic heart disease as well PAH. Macroscopic disappearance of the ischemic zone confirmed with low myocardial apoptosis and that despite permanent ligation of the coronary artery means improved hemodynamic is more related to open myocardial microcirculation in neonate animal model known with poor coronary collaterals.

A significant drop in the pulmonary vascular resistance was the key of hemodynamic improvement. There can be induced with our pulsatile systems after short period of intermittent shear stress-mediated endothelial function stimulations at the splanchnic and hepatic venous capacitance, or at the pulmonary artery, and irrespective to heart rate.

Pulsatile suit concept results that have been obtained in volunteers also open a new era of therapeutic approach in nearly all types of endothelial dysfunctions pathogenesis as follows:

Type A: endothelial dysfunction manifested with heart failure.

Type B: in endothelial dysfunction with normal heart function (e.g. diabetic, erectile dysfunction, systemic arterial hypertension, etc).

Type C: prophylactic in healthy individuals, liable for endothelial dysfunction pathogenesis (e.g. Astronauts, bedridden, etc) as well as a circulatory-hemodynamic physiological stimulus (e.g. athletics, anti-aging medicine, etc).

A current study of pulsatile trouser, is curried on in a CHF patient, who was short listed for heart and kidney transplant, then been removed due to severe sever PAH (systolic PAP>85 mmHg). In CHF patients trouser (with integrated belt) it is preferred to be used in a standing position, rather than supine position to amplify the gravity effect as an enhancement factor of shear stress with more voluminous columns of venous capacitance.

The pulsatile mask can improve the cerebral circulation directly through the cavernous venous systems, and systemically through the jugular venous system, current studies show enhancement of the retinal artery flow as well as diameter, which can be effective in treating neurodegenerative diseases and stroke patients.

This improvement is observed at points remote from the pulsating zone, i.e. where the suit was being worn.

A clear improvement in microcirculation has also been observed at the fingertips as a result of putting a pulsatile suit 100 on the bottom portion of a patient's body, as shown in FIG. 1.

Similarly, an improvement in the microcirculation of the myocardium has been observed in an ischemic model by ligating the left anterior descending coronary artery (LAD), after applying shear forces generated by a pulsatile catheter inserted in the pulmonary artery forming part of the right circuit of the heart.

Given the very short lifetime of nitric oxide, it cannot reach zones that are remote from the site where it is secreted, since it is necessarily absorbed by hemoglobin before reaching said remote zones. Thus, it has been found that at least one mediator mechanism other than those that are already known (such as nitrogen monoxide) and secreted by the endothelium is capable of triggering the opening of microcirculation. The devices and methods of the present disclosure advantageously enables such secretion to take place.

In known manner, the prior art constituted in particular by circulatory assistance systems such as LVAD, RVAD, artificial heart, etc., simulate the ventricular pump by complex driver forces.

In a manner that is very different, and indeed that is opposite in the physical sense of the word, the devices and methods of the present disclosure are designed to maintain circulation in the columns of blood within their own physiological containers as constituted by veins 6, 7, 8, 9 and arteries 1, 2, 3, 4, 5. The idea is to maintain a pulsatile blood stream complying with the biophysical and physiological standards of pulmonary and systemic circulation, by applying mechanical endothelial stimuli of shear stress.

One aspect of the devices and methods of the present disclosure enables shear stress endothelial stimuli to be increased, thereby enabling a microcirculation opening to be created in various organs of the human body by means not only of conventional mediators of vasodilators such as nitric oxide, but also by means of other new vasodilators processing.

Thus, the devices and methods of the present disclosure improve microcirculation and makes it possible to obtain other mediators of vasodilators produced by the endothelium by means of the devices used.

In one of the aspects of the present disclosure, blood is compressed from the outside of the body by means of a special suit 100 referred to as a "pulsatile" suit, of the kind described in patent application WO 2010/070018, which suit is used primarily to provide circulatory assistance to the right heart and secondarily as a device that makes it possible to obtain an overall hemodynamic improvement.

Figure 2:
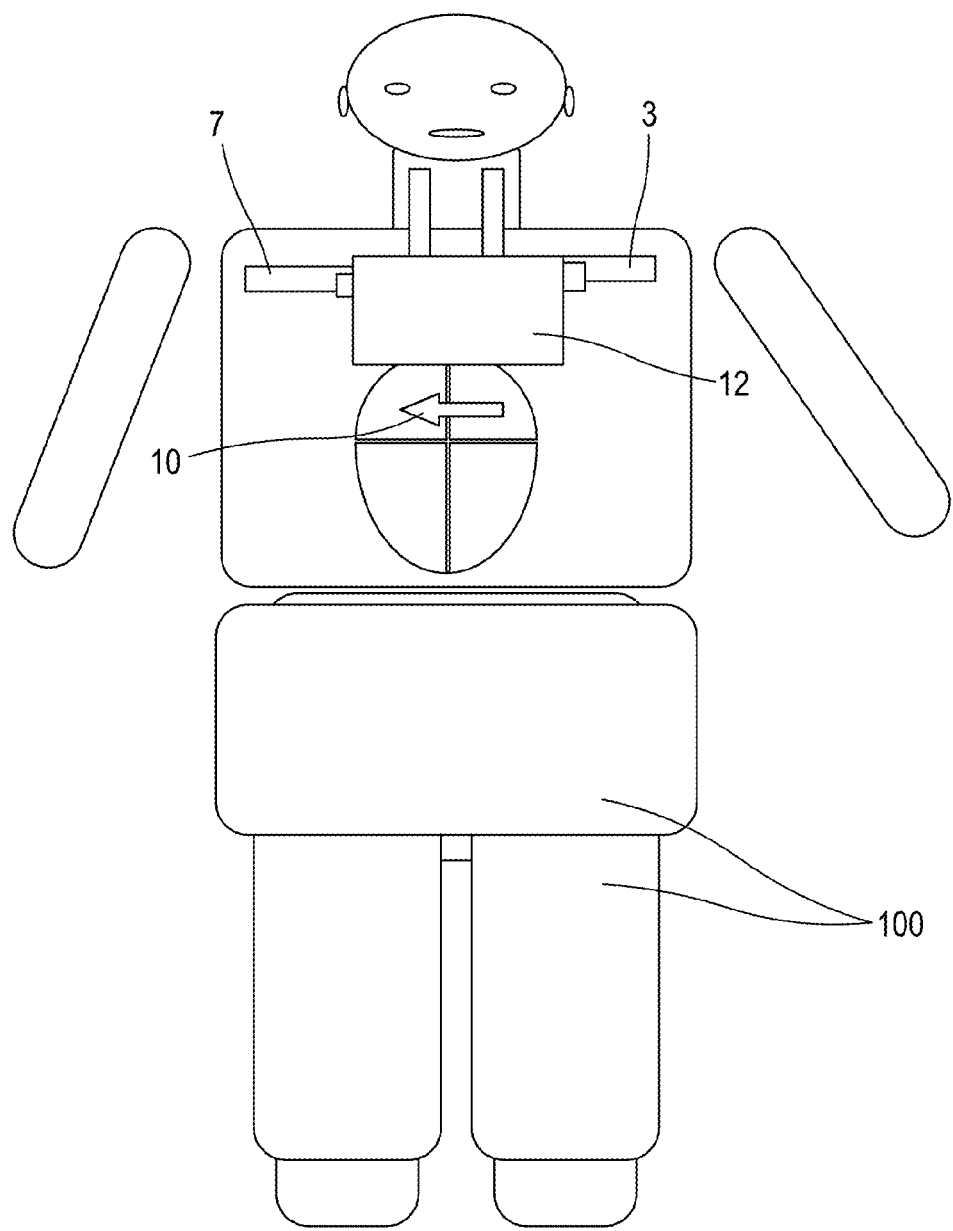
FIG. 2 is a diagrammatic section of equipment in a second aspect of the invention.

FIGS. 1 and 2 show such a suit 100 covering the bottom portion of the human body, which the therapist (doctor, nurse, or even patient) can put into place without effort. The suit may be connected directly to an external pump 110 as can be seen in FIG. 1; it may be actuated by the therapist himself or herself. Naturally, this pulsatile suit 100 may take on various forms such as a hood, a pair of trousers, a jacket, a glove, a boot, or a sock. The structure serves advantageously to guide the pulsations it generates, progressively in the venous return direction. It thus constitutes a circulatory assistance device for the right ventricle (RVAD).

In another of its aspects shown in FIG. 1, the invention implements at least one specific "pulsatile" pipe 12 that serves to impart pulses to columns of blood, and that is preferably used in the context of providing circulatory assistance to the left ventricle (LVAD). Such a pipe is described in particular in patent application WO 2010/066899. It may form part of a pulsatile medical kit that also includes a conventional pump 13 (with or without oxygenator) placed at one end of the pipe 12, and an aortic cannula 14 placed at the other end of the pipe 12. The aortic cannula is placed by the surgeon as close as possible to the patient's aorta. It is preferably prefilled in its intermediate space with an inert fluid such as helium, $CO_2$, etc. This diminishes the risk of embolism since the gas initially present in the pipe is discharged outside the circulation. In addition, the pressure forces required for operating the pulsatile device are reduced.

It can readily be understood that this device is invasive to a very small extent. It generates pulsations in most effective manner and it is very easy to implement. It may be put into place surgically via a mini-incision or via a percutaneous approach and then synchronized with the patient's electrocardiogram.

Furthermore, the pulsatile pipe 12 serves to reduce the empty space between the monitor system and the tube itself, thereby giving rise to optimized operation with minimum pulsatile pressure; it is thus possible to envisage miniaturizing the device and correspondingly reducing the energy needed for its operation.

As shown in FIG. 2, a pulsatile pipe 12 may be placed between the left subclavian artery 3 and the right subclavian vein 7.

Another aspect of the present disclosure comprises a "pulsatile" catheter comprising a conventional catheter that is surrounded by an inflatable element over a portion of its length. Such a catheter is disclosed in French patent application FR 2 929 523. Advantageously, the inflatable element in place around the catheter presents in the deflated state an outside diameter that is less than that of the remainder of the catheter. Naturally, the inflatable element is connected to external inflation means suitable for generating pulsations during inflation. The device advantageously makes it possible to avoid excessively enlarging of the point where the catheter is inserted into a blood vessel.

Such a device is used in particular for pulmonary hypertension with an increase in the afterload of the right ventricle (right ventricular failure); the catheter is placed in the trunk of the pulmonary artery by a percutaneous venous approach, preferably in association with a pulsatile suit.

An example of a pulsatile console 13, 110 is described in French patent application FR 2 931 680. That console is very simple in design and easy to use. The console enables determined pulsatile pressure to be created and applied to a pipe, a catheter, or any other equivalent means. A simple source of fluid under pressure such as a bottle of an inert fluid, or of liquid under high pressure constitutes the continuous source that is transformed into a pulsatile source by the pulsatile console as disclosed therein.

The various devices (pulsatile pipe, suit, and catheter, in particular) implemented in the present disclosure are synchronized together or separately as a function of the patient's hemodynamic parameters. Heart rhythm is detected by the electrocardiogram or by a pacemaker as a function of variation in arterial pressure and/or in systemic and pulmonary resistances.

All of those pulsatile means enable variations in blood pressure to be created in vessels in application of the physical laws that apply to non-Newtonian fluids. They allow stagnant blood to be moved in compliance with Bernoulli's law, i.e. from the walls towards the insides of the vessels. This therefore gives minimizes the traumatic effects on erythrocytes. In particular, the devices and methods of the present disclosure avoids problems associated with blood circulation through two well-separated circuits (systemic and pulmonary) that are constituted by the vessels and arteries of the patient and by the mechanical circulatory assistance device(s).

According to yet another aspect of the present disclosure, a secure and almost non-invasive connection is provided between the patient and external mechanical systems for providing circulatory assistance. This aspect may be achieved by a device of the kind described in French patent application FR 10/50428 filed on Jan. 22, 2010. That device makes it possible advantageously to group together all of the tools that make it possible to obtain a cardiovascular approach that is effective, fast, safe, and inexpensive. Thus, the tool enables a single operator to penetrate blood vessels and/or cardiac cavities. That tool, which may be put into place and fastened surgically by a single operator, makes it possible to avoid all of the traditional steps such as incision, suture stitches, purse strings. That simplifies the operation. Operating costs are thus significantly reduced.

Such a tool may be put into place and moved with assistance and remote guidance, e.g. echocardiography. This avoids blind guidance under the patient's skin for connecting the patient with an external circulatory assistance machine as with prior art methods. Such a connection gives rise to complications for the patient such as infections, hemorrhages, problems of closing the chest, etc.

In an advantageous manner, such a tool can be used as an aortic cannula, a cardiac cannula, a vascular catheter, or indeed as tubing for cavity drainage.

Such a tool, and more precisely the body of the device, is preferably prefilled with a liquid such as heparinized serum in order to reduce the risks of gaseous embolism and in order to shorten operating time. The cannula, catheter, etc. type systems used in the present disclosure are advantageously prefilled with a liquid; this serves to reduce the pressure force and to limit the risks of embolism; in addition, the energy needed for controlling and monitoring the systems is reduced.

In novel and advantageous manner, the distance between such a tool and the patient is very small. In other words, the distance between a circulatory assistance machine (referred to as a CAD) and the puncture sites (on the patient) is very short; in particular when implantation is performed close to the subclavicular artery. This characteristic greatly reduces the energy losses that are inherent to existing devices.

Thus, the surgeon implements at least one of these non-invasive devices in the context of therapeutic and/or surgical treatments, and interventions intended specifically for improving hemodynamics, and for restoring and preserving the endothelial function in a patient.

A pulsatile suit 100 is preferably placed on the patient prior to using other devices for improving overall hemodynamics by lowering pulmonary afterload.

When the heart pump, and in particular the left ventricle, is to be relieved (unloaded), the practitioner will use a device as disclosed in French patent application FR 10/50428 in a version that enables an incision via the tip of the left ventricle or a left intra-atrial transeptal incision.

Similarly, when regular pulsations are to be produced and diffused close to the aortic root, the same device may be inserted as an arterial perfusion cannula in the root of the aorta 2 or in the subclavian artery 3 via a percutaneous approach or by echocardiographic guidance.

Figure 3:
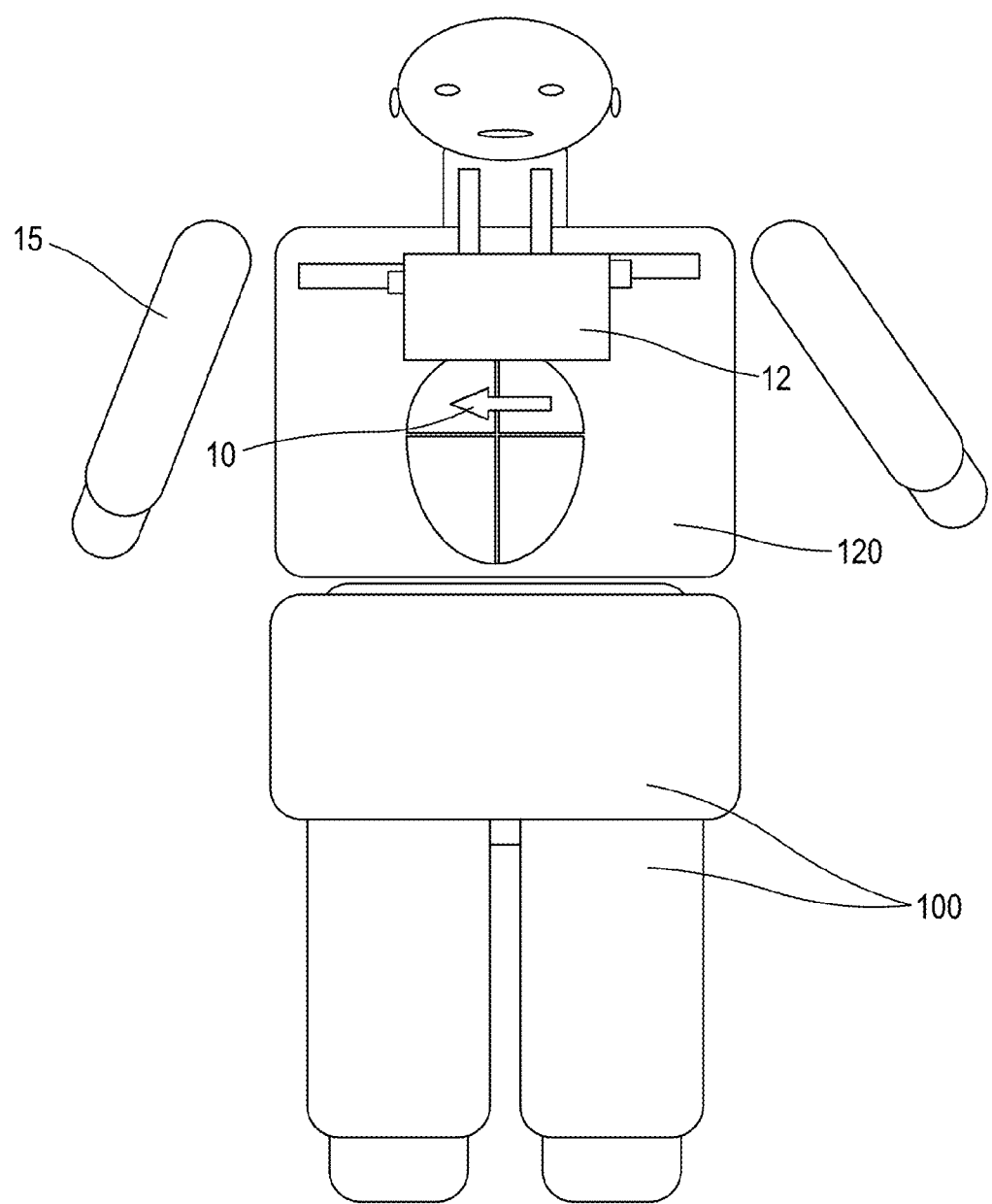
FIG. 3 is a diagrammatic section of equipment in a third aspect of the invention.

FIG. 3 shows a patient fitted with a pulsatile suit 100 that covers the bottom portion of the body; in addition, a pulsatile jacket 120 is placed around the patient's thorax and pulsatile sleeves 15 are placed on each of the patient's upper limbs. In this embodiment of the invention a pulsatile pipe is placed between the subclavian artery 3 and the subclavian vein 7.

In addition, the present invention is adapted to all age categories, from newborns to patients of great age and/or patients that are the most clinically fragile.

The present invention is suitable for managing various types of heart failure, regardless of the right or left etiology.

On the right heart, by putting pulsatile suit into place, the present invention makes it possible to reduce the stagnation of venous capacities; by implementing a pulsatile catheter, it is possible to reduce the pulmonary afterload.

On the left heart, putting a pulsatile pipe into place enables physiological pulse pressure to be maintained and directly serves to improve overall hemodynamics by reducing systemic afterload.

As a priority, assistance should be provided to the right portion of the heart. It is known that the right heart "dominates" the left heart and controls hemodynamics by pulmonary resistance. Isolated ventricular assistance, on the left or the right, can then be envisaged in accordance with the present disclosure; and after that assistance for the left heart.

Thus, the methods and devices according to the present disclosure may be defined as a circulatory orthosis, as opposed to a prosthesis. Unlike orthotopic transplantation, the present disclosure makes it possible to keep the patient's heart in place, thus allowing the patient to wait in relative comfort for a histocompatible donor. The present method provides bridging treatment prior to transplantation, thereby improving prognosis and morbidity by restoring the patient's hemodynamics. As a reminder, present-day mortality is high for right ventricular failure it lies in the range 65% to 95%.

The present disclosure makes it possible to restore the endothelial function progressively by maintaining quasi-physiological shear forces on the endothelium; consequently, there is a significant improvement in the function of the myocardium, thus making it possible to avoid subsequent transplants.

The present disclosure complies with the patient's hemodynamic parameters as a function of breathing frequency and cardiac rhythm. Synchronizing the pulsatile suit, thereby increasing venous return (preload) and reducing afterload, needs to be performed without hindering the frequency of breathing and without increasing central venous pressure above 16 millimeters of mercury (mmHg). The pulsatile frequency of the suit may be less than the cardiac frequency of the patient (one-third to two-thirds of the heart beat). In contrast, the pulsatile pipe associated with the patient's electrocardiogram may be synchronized with cardiac rhythm and the pulsatile catheter may be faster than heart rate.

The present disclosure provides an approach that is invasive to a very small extent, since it avoids risky surgical acts, in particular on patients who have already been operated on and who are fragile; in particular, the invention avoids sternotomy and/or thoractomy which can be put off until subsequent transplantation.

The devices and method of the present disclosure thus makes it possible to cope with the shortage of donors and with the numerous problems that are associated with antirejection treatments.

What is claimed is:

1. A therapeutic method for improving overall microcirculation in organs, for improving hemodynamics, for restoring and preserving deficient endothelial function in a diseased patient, the method comprising:
    maintaining circulatory flow dynamics of blood in systemic and pulmonary circuits of the diseased patient; and
    temporarily relieving a pumping function of a heart of the diseased patient;
    wherein the method further comprises using at least one device external to a body of the diseased patient and connected via a connection element, to:
    increase a preload of a right ventricle of the heart so as to improve myocardium oxygenation and its contractility; or
    unload a left ventricle of the heart and diffuse regular pulsatile flow in a proximity of an aortic root of the heart so as to improve hemodynamics of the left ventricle; or
    stimulate an endothelium of the diseased patient mechanically by shear stress enhancement so as to reduce afterload of the systemic and pulmonary circuits and release several mediators of endothelial vasodilators, in such a manner as to improve microcirculation of main vital organs of the diseased patient by means of the several endothelial vascular vasodilators mediators secreted in particular in response to an application of quasi-physiological tangential forces of shear stresses on endothelial walls of the diseased patient.

2. The method according to claim 1, wherein regular pulsations created in the proximity of the aortic root are synchronized with the patient's electrocardiogram.

3. The method according to claim 1, wherein disturbances of the angiogenesis-apoptosis interdependency processes that are degraded in the patient are restored.

4. The method according to claim 1, wherein the step of temporarily relieving the heart consists in relieving the left ventricle.

5. The method according to claim 4, wherein said relief is performed starting from an apex of said left ventricle.

6. The method according to claim 4, wherein said left ventricle relief is performed by a transeptal left atrial approach.

7. The method according to claim 1, wherein said pulsations are diffused in the proximity of the aortic root by inserting a perforation cannula in the aortic root or in the subclavian artery, by a percutaneous approach, optionally assisted by remote guidance such as echocardiogram guidance.

8. The method according to claim 1, wherein functional relief of the left ventricle is performed by inserting a cannula by a percutaneous approach, preferably guided by echography, into the fifth intercostal space or into a large systemic vein.

9. The method according to claim 1, wherein at the beginning of the surgical procedure, the connection element is filled with heparinized physiological saline so as to avoid any form of gaseous embolism during or after said method.

10. The method according to claim 1, wherein a pulsatile intra-pulmonary catheter is put into place by a percutaneous venous approach so as to reduce pulmonary afterload and improve microcirculation and contractility.

11. The method according to claim 1, wherein a pulsatile suit is put into place on a portion of the patient's body so as to improve the functioning of the right ventricle and also the hemodynamics of said patient.

12. A therapeutic method for improving overall microcirculation in organs, improving hemodynamics, and restoring and preserving deficient endothelial function in a patient, the method comprising:
    maintaining circulatory flow dynamics of blood in systemic and pulmonary circuits of the patient; and
    temporarily relieving a pumping function of a heart of the patient in such a manner as to improve microcirculation of main vital organs of the patient by means of a plurality of endothelial vascular vasodilators mediators secreted in particular in response to an application of quasi-physiological tangential forces of shear stresses on endothelial walls of the patient, wherein the method further comprises using at least one device external to a body of the diseased patient and connected via a connection element.

13. The method of claim 12, wherein the external device increases a preload of a right ventricle of the heart so as to improve myocardium oxygenation and its contractility.

14. The method of claim 12, wherein the external device unloads a left ventricle of the heart and diffuses regular pulsatile flow in a proximity of an aortic root of the heart so as to improve hemodynamics of the left ventricle.

15. The method of claim 12, wherein the external device stimulates an endothelium of the heart mechanically by shear stress enhancement so as to reduce systemic and pulmonary afterload and release the mediators of endothelial vasodilators.

16. A therapeutic method for improving overall microcirculation in organs, improving hemodynamics, and restoring and preserving deficient endothelial function in a patient, the method comprising:
    improving oxygenation of a myocardium of the patient by increasing a preload of a right ventricle of the patient and improving its contractility;
    unloading a left ventricle of the patient and diffusing regular pulsatile flow in a proximity of an aortic root of the patient so as to improve hemodynamics of the left ventricle of the heart; and stimulating the patient's endothelium mechanically by shear stress enhancement so as to reduce systemic and pulmonary afterload and so as to release a plurality of mediators of endothelial vasodilators, in a manner sufficient such that microcirculation of the main vital organs of the patient is improved by the plurality of endothelial vascular vasodilators mediators secreted in response to an application of quasi-physiological tangential forces of shear stresses on endothelial walls of the patient.

* * * * *